US00PP30624P2

(12) United States Plant Patent
de Geus et al.

(10) Patent No.: US PP30,624 P2
(45) Date of Patent: Jul. 2, 2019

(54) ***ROSA* PLANT NAMED 'ELIZABETH ASHLEY'**

(50) Latin Name: ***Rosa* hybrid**
Varietal Denomination: Elizabeth Ashley

(71) Applicant: Elizabeth Ashley Hoke Memorial Trust, Silverton, OR (US)

(72) Inventors: Dennis de Geus, Noord (NL); Michael de Geus, Barger-Compascuum (NL)

(73) Assignee: ELIZABETH ASHLEY HOKE MEMORIAL TRUST, Silverton, OR (US)

( * ) Notice: Subject to any disclaimer, the term of this patent is extended or adjusted under 35 U.S.C. 154(b) by 0 days.

(21) Appl. No.: 15/932,968

(22) Filed: May 31, 2018

(51) Int. Cl.
*A01H 5/02* (2018.01)

(52) U.S. Cl.
USPC ..... Plt./132
CPC ..... *A01H 5/02* (2013.01)

(58) Field of Classification Search
USPC ..... Plt./132, 130
CPC ..... A01H 5/0222
See application file for complete search history.

*Primary Examiner* — Kent L Bell
(74) *Attorney, Agent, or Firm* — Penny J. Aguirre

(57) ABSTRACT

A new cultivar of *Rosa* plant named 'Elizabeth Ashley' that is characterized by its compact, upright, and uniform plant habit, its double flowers that are bi-colored with yellow-orange and dark red-pink petals, its glossy and disease-free foliage, and its continuous and prolific blooming habit.

2 Drawing Sheets

Botanical classification: *Rosa* hybrid.
Variety denomination: 'Elizabeth Ashley'.

BACKGROUND OF THE INVENTION

The present invention relates to a new and distinct cultivar of *Rosa* hybrid. The new cultivar will be referred to hereafter by its cultivar name, 'Elizabeth Ashley'. 'Elizabeth Ashley' is a new cultivar of hybrid tea rose grown for use as a container and landscape plant.

'Elizabeth Ashley' was derived from controlled crosses made in May of 2011 in Klazienaveen, The Netherlands between unnamed and unpatented *Rosa* plants from the Inventor's breeding program as both the male and female parents. Seeds were pooled from various crosses and therefore the exact parent plants are unknown. 'Elizabeth Ashley' was selected in January of 2012 as a single unique plant amongst the resulting seedlings from the above crosses.

Asexual propagation of the new cultivar was first accomplished by softwood stem cuttings by one of the Inventors in October of 2012 in Klazienaveen, The Netherlands. Asexual propagation by softwood stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Elizabeth Ashley' as a unique cultivar of *Rosa*.

1. 'Elizabeth Ashley' exhibits a compact, upright and uniform plant habit.
2. 'Elizabeth Ashley' exhibits double flowers that are bi-colored with yellow-orange and dark red-pink petals.
3. 'Elizabeth Ashley' exhibits glossy foliage.
4. 'Elizabeth Ashley' exhibits disease free foliage.

5. 'Elizabeth Ashley' exhibits a continuous and prolific blooming habit.

'Elizabeth Ashley' can also be compared to the *Rosa* cultivars 'BAIpeace' (U.S. Plant Pat. No. 14,731), 'WEKdocpot' (U.S. Plant Pat. No. 20,633), and 'Mein München' (not patented). All are similar to 'Elizabeth Ashley' in flower coloration. 'BAIpeace' differs from 'Elizabeth Ashley' in having a taller plant height, in having leaves that are less glossy, in having flower buds that are larger in size and in producing less flowers. 'WEKdocpot' differs from 'Elizabeth Ashley' in having larger flowers. 'Mein München' differs from 'Elizabeth Ashley' in having flowers with fewer and larger flower buds, deeper flower coloration and in having a less compact plant habit.

BRIEF DESCRIPTION OF THE DRAWINGS

The accompanying colored photographs illustrate the overall appearance and distinct characteristics of the new *Rosa*. The photographs were taken of a two-year-old plant of 'Elizabeth Ashley' as grown in a greenhouse in a 2-gallon container Klazienaveen, The Netherlands.

The photograph in FIG. 1 provides a side view of a plant of 'Elizabeth Ashley' in bloom.

Figure 1:
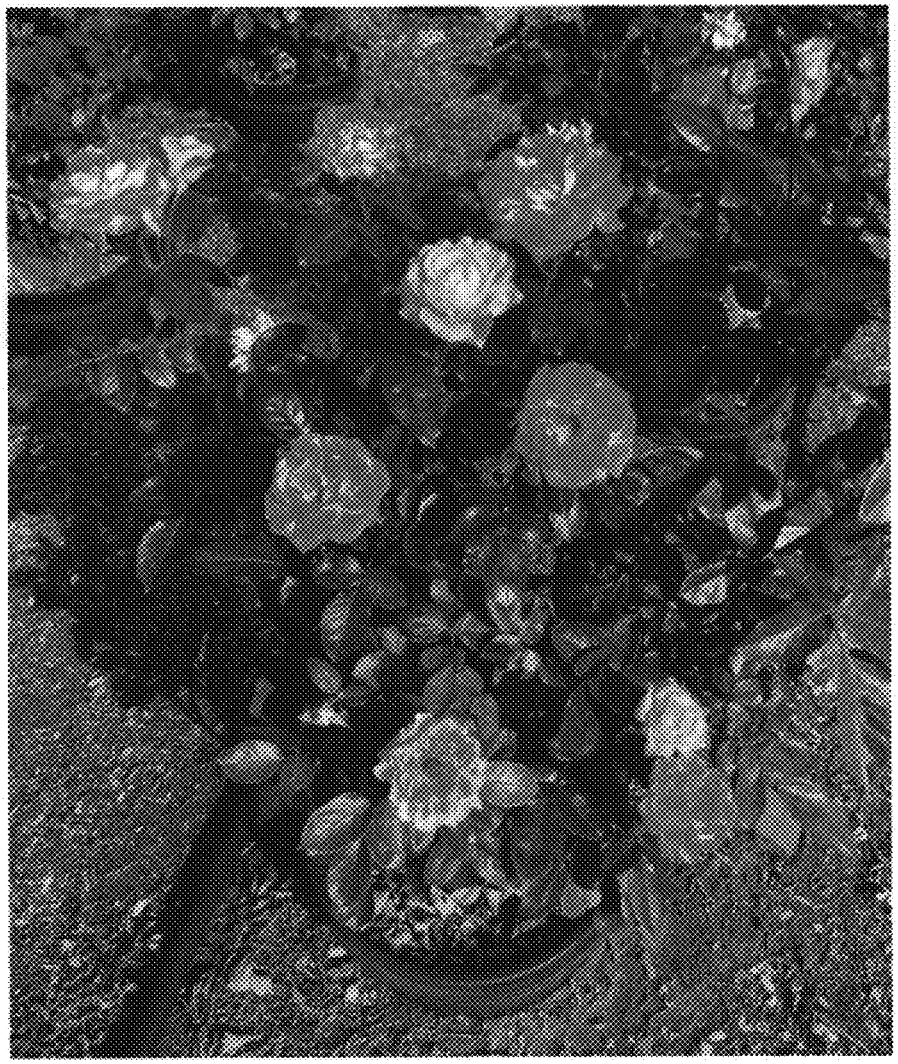
Figure 2:
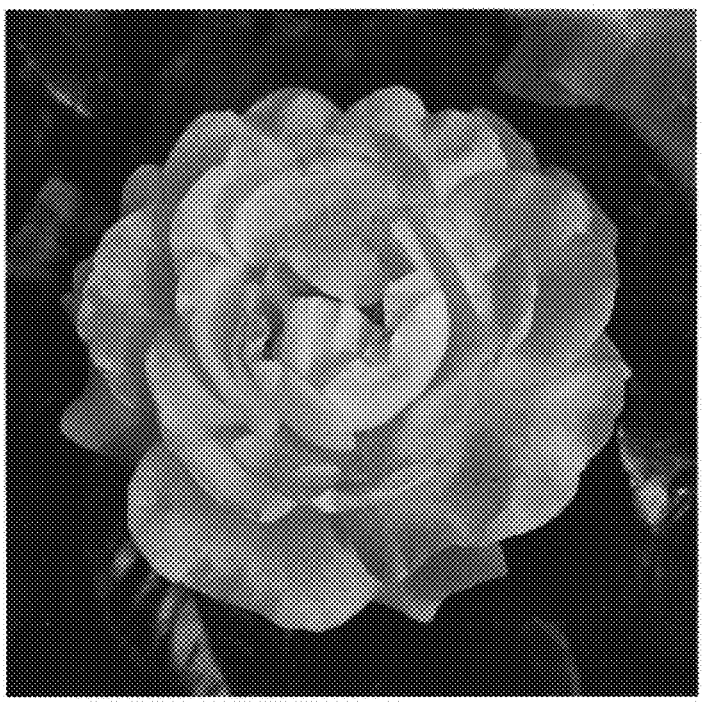

The photograph in FIG. 2 provides a close-up view of a newly opened flower of 'Elizabeth Ashley'.

Figure 3:
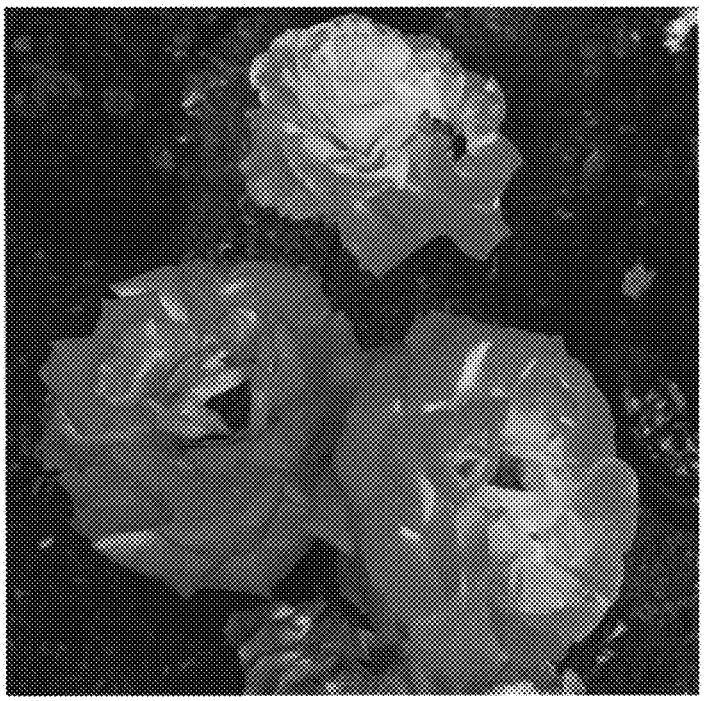

The photograph in FIG. 3 provides a close-up view of multiple flowers in different maturation stage of 'Elizabeth Ashley'.

The colors in the photographs are as close as possible with the photographic and printing technology utilized and the color values cited in the Detailed Botanical Description accurately describe the colors of the new *Rosa*.

DETAILED BOTANICAL DESCRIPTION

The following is a detailed description of 4-year-old plants of 'Elizabeth Ashley' as grown in a greenhouse in #6 containers in Salem, Oreg. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—From June to September in The Netherlands.

*Plant type.*—Herbaceous perennial.

*Plant habit.*—Compact, upright and uniform.

*Height and spread.*—Reaches an average of 80 cm in height and 40 cm in spread in the landscape.

*Cold hardiness.*—At least to U.S.D.A. Zone 8a.

*Diseases.*—Plants have been observed to be healthy and free from diseases rose black spot (*Diplocarpon rosae*) and rose powdery mildew (*Podosphaera pannosa*) however comparison trials for resistance have not been conducted.

*Root description.*—Fibrous and fine, 161D in color.

*Root development.*—An average of 5 weeks for root initiation with a young rooted plant produced in 10 weeks from a rooted cutting.

*Propagation*—Softwood stem cuttings.

*Growth rate.*—Moderate.

Branch description:

*Stem shape.*—Round and very slightly oval on new growth.

*Stem color.*—Young; 146C, maturing and mature stems; 146A and very slightly tinged with 165A, bark; 146A with fissures of 200D and 200A.

*Stem surface.*—Young and mature stems; glabrous, smooth, and satiny, mature wood; glabrous and finely barked with fissures.

*Stem size.*—Main branches; ranges from 5 mm to 1.5 cm in width and 20 cm in length (trimmed before new growth), lateral branches; an average of 5 mm in width and 30 cm in length.

*Branching.*—An average of 4 main branches and average of 2 lateral branches per main branch.

*Thorns.*—Sparsely distributed on new growth and more densely on second year stems with an average of 7 per new branch 20 cm in length and 20 per second year wood 6 cm in length, elongated triangle in shape, held outward to slightly downwards, oval base, entire margin, narrowly acute apex, 1 cm in length with a base 8 mm in length and 3 mm in width, 183A to 183B in color on new growth and a blend of 200D and 199D in color on second year stems.

Foliage description:

*Leaves.*—Odd-pinnate division, alternate arrangement, an average of 15.5 cm in length and 8.5 cm in width, internode length is an average of 3.75 cm.

*Leaflets.*—5 to 7 per leaf (occasionally 3), oval to elliptic in shape, rounded to slightly cuneate base, acute to slightly acuminate apex, serrate margins, apical leaflet; an average of 5.7 cm in length and 4.4 cm in width, lateral leaflets; an average of 4 cm in length and 3 cm in width, color; emerging growth 146A and suffused with a color between 187B and N77A (more heavily at margins), on young leaves a blend of 144A and 137A on upper surface with very margin N77A and 138B on lower surface with very margin N77A, mature leaves upper surface 139A and lower surface N138B, veins on mature leaves; pinnate, not conspicuous and color 144A on upper surface and 191B on lower surface, surface upper surface glabrous, smooth, and glossy and lower surface; glabrous, smooth, and dull.

*Rachis.*—An average of 11.5 cm in length and 1.5 mm in diameter, color; upper surface 146B and suffused with 187A and lower surface 146B, surface glabrous and smooth on upper and lower surface with upper surface slightly sulcate.

*Stipules.*—Held outward with auricles facing upright, adnate to petiole, an average of 1.7 cm in length and 4.5 mm in width, color upper and lower surface; 138A and occasionally slightly suffused with 183A, both surfaces glabrous and smooth.

*Petioles and petiolules.*—Petioles; an average of 3 cm in length (including stipule) and 1.5 mm in width, apical petiolules; an average of 2 cm in length and 1.5 mm in width, lateral petiolules; an average of 1.5 mm in length and width, petioles and petiolules; color upper surface 146B and suffused with 187A and lower surface 146B, both surfaces glabrous and smooth.

Inflorescence description:

*Inflorescence type.*—Solitary rosette-formed double flowers present at the stem apices.

*Flower number.*—An average of 1 per lateral stem.

*Flower fragrance.*—Light pleasant, sweet rose scent.

*Flower longevity.*—10 to 12 days, depending on temperature and sunlight exposure.

*Flower type.*—Double solitary symmetrical rosettes, flattened and round in shape.

*Flower size.*—An average of 8.2 cm in diameter and 5.5 cm in depth (excluding refluxed sepals.

*Flower aspect.*—Upwards.

*Peduncles.*—Slightly oval in shape, an average of 7.5 cm in length and 4 mm in diameter, surface glossy with sparse prickles and or hairs, 146C in color and occasional slightly suffused with 183A with prickles and hairs 162D in color.

*Bracts.*—None observed.

*Flower buds.*—Ovate in shape, an average of 4.4 cm in length and 3.2 cm in width prior to opening, color 7A with petal margins 34B and sepal color matching mature flowers.

*Sepals.*—5, lanceolate in shape, entire margin often with 0 to 3 very fine leafy appendages; about 4 mm in length and 0.7 mm in width, acuminate apex, truncate base, an average of 3.8 cm in length and 1.2 cm in width 146A in color, surface glabrous, color; upper and lower surfaces 138A with 146D in center at base and upper surface suffused in center with 182B, margins on both surfaces 161D, reflexed towards stem on mature flowers, surface upper surface densely pubescent, lower surface glabrous, margins wooly.

*Petals.*—An average of 29 per flower, rounded to obovate (more obovate in center of flower) in shape, slightly wavy margins, slightly cuneate base, rounded apex with outer petals retuse, outer petals (13); an average of 4 cm in length and 4.3 cm in width, inner petals; an average of 2.8 cm in length and width, color; opening upper surface 13A and suffused on margins with 34B and lower surfaces;

13A, glabrous, color mature flowers upper surface 13B and heavily suffused with 34B with a few specks of 155A as the flower fades and lower surface 13C with 34B on some apical margins, surface smooth, and velvety on upper and lower surfaces, basal spot absent.

*Receptacle* (*hypanthium*).—Round in shape with apex flat with tubular around margins, an average of 1 cm in diameter and depth, glabrous and shiny surface, a blend of 138A and 138B in color with apex 3A in color.

Reproductive organs:

*Gynoecium.*—About 35 pistils per flower, stigma; an average of 1 mm in length, 3A in color, style; an average of 1 cm in length and 0.5 mm in width, 1D in color, pubescent with long hairs about 155A in color, ovary is narrow oblong in shape, an average of 4 mm in length and 1.5 mm in width, 1D in color and very pubescent with long (up to 5 mm in length) fine hairs about 155A in color.

*Androecium.*—An average of 100 stamens, filaments; up to 1 cm in length and 13A in color, anthers; basifixed, an average of 2 mm in length and 1 mm in width, and 13A in color, pollen was moderate to abundant in quantity and 17A in color.

*Hips.*—Globose with a flat apex in shape, an average of 1 cm in width and height, 138A in color when immature, surface is dull.

It is claimed:

1. A new and distinct cultivar of *Rosa* plant named 'Elizabeth Ashley' as herein illustrated and described.

* * * * *